United States Patent [19]

White et al.

[11] 4,451,465

[45] May 29, 1984

[54] ANTI-OBESITY AGENTS

[75] Inventors: Alan C. White, Windsor; Michael G. Wyllie, Maidenhead, both of England

[73] Assignee: John Wyeth & Brother Ltd., Maidenhead, England

[21] Appl. No.: 391,071

[22] Filed: Jun. 22, 1982

[30] Foreign Application Priority Data

Jul. 7, 1981 [GB] United Kingdom ................. 8120961

[51] Int. Cl.³ ........................................... A61K 31/505
[52] U.S. Cl. .................................................. 424/251
[58] Field of Search ......................................... 424/251

[56] References Cited

U.S. PATENT DOCUMENTS 4,307,234  12/1981  Jirkovsky ............................ 424/251

FOREIGN PATENT DOCUMENTS 2200584  7/1972  Fed. Rep. of Germany .
1366133  9/1974  United Kingdom .

Primary Examiner—Douglas W. Robinson
Attorney, Agent, or Firm—Arthur G. Seifert

[57] ABSTRACT 2,3,4,10-Tetrahydro-3,3-dimethyl-10-phenyl-pyrimido[1,2-a]indol-10-ol and the pharmaceutically acceptable acid addition salts thereof are useful in treatment or preventing obesity in mammals. The compounds may be administered in pharmaceutical compositions, optionally with one or more vitamins.

3 Claims, No Drawings

ANTI-OBESITY AGENTS

This invention relates to anti-obesity agents and their use in preventing or treating obesity in mammals, particularly humans.

Hitherto the usual method employed to treat obesity in man has been to reduce the intake of food either by a low calorie diet or by the use of appetite suppressant (anorexic) agents or by a combination of the two. The anorexic agents are, in general, not entirely satisfactory since either they do not remain effective for the long periods that are necessary to achieve the necessary loss of weight or they possess undesirable side effects, in particular central stimulatory effects. We have now found an anti-obesity agent which is believed to produce weight loss by a mechanism other than suppressing the appetite. (e.g. by peripheral burning off of energy).

According to the present invention there is provided a method of treating or preventing obesity in mammals which comprises administering to the mammal in need thereof an effective amount of 2,3,4,10-tetrahydro-3,3-dimethyl-10-phenylpyrimido[1,2-a]indol-10ol or a pharmaceutically acceptable acid addition salt thereof. The mammal is preferably a human. The invention also provides 2,3,4,10-tetrahydro-3,3-dimethyl-10-phenylpyrimido[1,2-a]indol-10-ol or a pharmaceutically acceptable acid addition salt thereof for use as an anti-obesity agent.

The preparation of 2,3,4,10-tetrahydro-3,3-dimethyl-10-phenylpyrimido[1,2-a]indol-10-ol and its acid addition salts is described in UK patent specification No. 1,366,133. For example, 3,4-dihydro-3,3-dimethyl-pyrimido[1,2-a]indol-10[2H]-one may be reacted with a phenyl lithium or a phenyl Grignard reagent, e.g. phenyl magnesium bromide. If required, a racemic mixture of the product may be resolved, by methods described in the literature, e.g. by resolving the base with an optically active acid, to give the product in the form of an optical isomer. (−)-2,3,4,10-Tetrahydro-3,3-dimethyl-10-phenylpyrimido[1,2-a]indol-10-ol and its pharmaceutically acceptable acid addition salts are particularly useful as anti-obesity agents being more active, as thermogenic agents, than the corresponding (+)-enantiomers. The pharmacologically active isomers may of course, be administered as mixtures with their enantiomers, especially as racemic mixtures.

The acid addition salts of the compounds may be isolated directly from the processes described above or prepared by dissolving the base in a suitable solvent and treating it with the selected acid in accordance with conventional procedures for preparing acid addition salts. Examples of pharmaceutically acceptable acid addition salts are those derived from inorganic and organic acids such as sulphuric, hydrochloric, hydrobromic, phosphoric, tartaric, fumaric, maleic, citric, acetic, formic, methanesulphonic and p-toluenesulphonic acids. A particularly preferred acid addition salt is the methanesulphonate (mesylate).

Pharmacological testing of the anti-obesity agents of the present invention has indicated that the compounds possess thermogenic activity and hence they are potentially useful as anti-obesity agents by a mechanism which is believed to involve specific stimulation of the metabolic rate by an action in brown adipose tissue.

In one procedure for testing for potential thermogenic activity the compounds are tested for their ability to inhibit noradrenaline uptake in rat brown adipose tissue (BAT). Compounds that have a specific thermogenic effect without having undesirable central effects should inhibit BAT noradrenaline (NA) uptake at lower concentrations than those required to inhibit corresponding NA uptake in the brain. In another procedure for testing for thermogenic activity the compounds are investigated for their effect on the activity of sodium potassium activated, magnesium dependent adenosine-triphosphatase ($Na^+$, $K^+$-ATPase) in rat BAT fractions.

In the above mentioned procedures adult male Sprague-Dawley rats were used. Homogenates of BAT were prepared by homogenising interscapular BAT. Microsomal material was separated by centrifugation of the BAT homogenate. Measurement of NA uptake into BAT and brain slices was carried out using radiolabelled noradrenaline (based upon the procedure of Sugden, Br. J. Pharmac., 1974,51, 467–469). Adenosine-triphosphate activities were measured by monitoring the release of inorganic phosphate from ATP. $Na^+$, $K^+$-ATPase was calculated as the difference between total and sodium ATPase.

The potencies for the inhibition of noradrenaline uptake in BAT and brian of (±)- and (−)-2,3,4,10-tetrahydro-3,3-dimethyl-10-phenyl-pyrimido[1,2-a]indol are given below:

| Isomer | IC$_{50}$ (M) BAT | Brain |
|---|---|---|
| (±) | $2.8 \pm 0.3 \times 10^{-8}$ | $3.4 \pm 0.3 \times 10^{-6}$ |
| (−) | $1.8 \pm 0.4 \times 10^{-8}$ | $2.4 \pm 0.2 \times 10^{-6}$ |

(values are the mean± S.E. mean of 6 experiments). These results clearly show that the compound of the invention is considerably more potent in inhibiting NA uptake into BAT than into brain slices indicating that the compound is likely to produce thermogenic activity in BAT without significant central effects.

The compound of the invention did not directly stimulate BAT microsomal $Na^+$, $K^+$-ATPase but there was significant stimulation of homogenate $Na^+$, $K^+$-ATPase as shown by the results below:

| Isomer | Effects on BAT $Na^+$,K-ATP-ase IC$_{50}$ for stimulation (to 50% maximum) Homogenate | Microsomal fraction |
|---|---|---|
| (±) | $4.3 \pm 0.5 \times 10^{-8}$ | none at $10^{-4}$ |
| (−) | $3.2 \pm 0.4 \times 10^{-8}$ | none at $10^{-4}$ |

The data shows that the concentration of the compound required to produce 50% of the maximal effect on the enzyme was similar to that required to inhibit NA uptake by 50%.

Recent data has shown that high metabolic rates of hyperphagic rats exhibiting diet induced thermogenesis and cold-adapted animals exhibiting nonshivering thermogenesis result from heat production in BAT (Rothwell and Stock, Pflugers Archiv., 1981 389, 237–241; Foster and Frydman, Can.J.Physiol., 1978, 56, 110). It is also known that there is a good correlation between BAT homogenate $Na^+$, $K^+$-ATPase activity and the resting metabolic rate (see, for example, Rothwell, Stock and Wyllie, Biochem. Pharmacol., 1981, 30, 1709–1712) and those compounds, such as the agents of the present invention that activate BAT $Na^+K^+$-

ATPase activity are indicated as useful as thermogenic agents and can be used in the treatment of obesity. It has been confirmed that the anti-obesity agent of the present invention increases the resting metabolic rate (as determined by resting oxygen consumption) in rats. The compound, however, did not produce signs of CNS arousal in rats (at dosages as high as 30 mg/kg p.o.).

The anti-obesity activity of (±)-2,3,4,10-tetrahydro-3,3-dimethyl-10-phenylpyrimido[1,2-a]indol-10-ol has been confirmed by chronic (28 day) administration to male rats. The animals were fed on a standard pelleted diet and the active agent was introduced into the water supply. Body weight, food and water intake and behaviour were monitored over the next four weeks. It was found that the active agent at 3.5 mg/kg/day and at 6.5 mg/kg/day reduced weight gain in rats compared to controls while at 10.8 mg/kg/day there was a weight loss. There was no significant effect on food intake indicating a thermogenic action for the active compound.

The active ingredients of the present invention may be administered alone or in the form of a pharmaceutical composition. The pharmaceutical compositions comprise 2,3,4,10-tetrahydro-3,3-dimethyl-10-phenylpyrimido[1,2,-a]indol-10-ol or a pharmaceutically acceptable salt thereof in association with a pharmaceutically acceptable carrier. The compositions may be prepared by a process which comprises bringing the active ingredient into association with the carrier (e.g. by mixing). Any suitable carrier known in the art can be used to prepare the pharmaceutical composition. In such a composition, the carrier is generally a solid or liquid, or a mixture of a solid and a liquid.

Solid form compositions include powders, granules, tablets and capsules (e.g. hard and soft gelatin capsules). A solid carrier can be, for example, one or more substances which may also act as flavouring agents, lubricants, solubilisers, suspending agents, fillers, glidants, compression aids, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99% preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups and elixirs. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweeteners, flavouring agents, suspending agents, thickening agents, colours, viscosity regulators, stabilisers, or osmo-regulators. Suitable examples of liquid carriers for oral administration include water (particularly containing additives as above e.g. cellulose derivatives, preferably sodium carboxymethyl cellulose solution): alcohols (including monohydric alcohols and polyhydric alcohols, e.g. glycerol and glycols) and their derivatives, and oils (e.g. fractionated coconut oil and arachis oil).

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form. The quantity of the active ingredient in a unit dose of composition may be varied or adjusted from 1 mg. or less to 750 mg. or more, according to the particular need and the activity of the active ingredient.

The dosage of the present agents will vary with the form of administration and the particular compound chosen. Furthermore, it will vary with the particular subject under treatment. Treatment may be initiated with small dosages substantially less than the optimum dose of the compound. Thereafter, the dosage may be increased by small increments until the optimum effect under the circumstances is reached. In general, the compounds of this invention are most desirably administered at a concentration level that will generally afford effective results without causing any harmful or deleterious side effects. In general a dose of 1 to 250 mg of the agent should be suitable for an average adult. Preferred oral recommended amounts are 5 to 150 mg. particularly 5 to 50 mg.

Administration of an anti-obesity agent of the present invention will often be accompanied by a diet regime and in these circumstances the anti-obesity agent may be administered with one or more vitamins in order to supplement those of the diet. Accordingly in one aspect of the invention there is provided a pharmaceutical composition comprising 2,3,4,10-tetrahydro-3,3-dimethyl-10-phenylpyrimido[1,2-a]indol-10-ol or a pharmaceutically acceptable acid addition salt thereof and one or more vitamins in association with a pharmaceutical carrier.

The following Examples 1 to 12 illustrate pharmaceutical compositions containing the anti-obesity agents of the present invention. Example 13 illustrates the preparation of optically active isomers of the anti-obesity agents.

EXAMPLES 1 TO 3

Capsules of the following compositions are made by screening batches of all the ingredients, mixing them together and filling hard gelatin capsules with the mixture:

|  | mg/capsule | mg/capsule | mg/capsule |
| --- | --- | --- | --- |
| 2,3,4,10-tetrahydro-3,3-dimethyl-10-phenyl pyrimido[1,2-a]indol-10-ol mesylate | 13.29 | 26.58 | 66.45 |
| Lactose | 54.46 | 108.92 | 136.80 |
| Maize starch (dried) | 30.0 | 60.0 | 90.0 |
| Aerosil 200 (colloidal | 2.0 | 4.0 | 6.0 |

|  | mg/capsule | mg/capsule | mg/capsule |
|---|---|---|---|
| silicon dioxide) | | | |
| Magnesium stearate BP | 0.25 | 0.5 | 0.75 |
| | 100 | 200 | 300 |
| [Hard gelatin capsules size:- | No. 5 | No. 3 | No. 1] |

EXAMPLES 4 TO 6

Tablets of the following compositions are made by screening and mixing the drug, lactose and Avicel. The mixture is wet granulated with water, dried and dry screened. The Explotab and magnesium stearate is mixed in and the mixture compressed into tablets:

| | Example 4 mg/tablet | Example 5 mg/tablet | Example 6 mg/tablet |
|---|---|---|---|
| 2,3,4,10-tetrahydro-3,3-dimethyl-10-phenyl-pyrimido[1,2-a]indol-10-ol mesylate | 13.29 | 26.58 | 66.45 |
| Lactose BP | 55.11 | 110.22 | 132.3 |
| Avicel pH 101 (microcrystalline cellulose) | 45.0 | 90.0 | 132.0 |
| Explotab (Sodium starch glycolate) | 6.0 | 12.0 | 17.50 |
| Magnesium stearate | 0.6 | 1.2 | 1.75 |
| | 120 | 240 | 350 |

EXAMPLES 7 TO 9

| Tablets | Example 7 10 mg base | Example 8 20 mg base | Example 9 50 mg base |
|---|---|---|---|
| 2,3,4,10-tetrahydro-3,3-dimethyl-10-phenyl pyrimido[1,2-a]indol-10-ol mesylate | 13.29 | 26.58 | 66.45 |
| Nicotinamide B.P. | 30.0 | 30.0 | 30.0 |
| Pyridoxine HCl B.P. | 2.0 | 2.0 | 2.0 |
| Riboflavine B.P. | 6.0* | 6.0* | 6.0* |
| Thiamine Hydrochloride B.P. | 7.5* | 7.5* | 7.5* |
| Tartaric acid B.P. (powder) | 1.0 | 2.0 | 2.0 |
| Lactose B.P. | 54.21 | 104.82 | 168.55 |
| Avicel pH 101 (microcrystalline cellulose) | 75.0 | 150.0 | 190.0 |
| Explotab (sodium starch glycolate) | 10.0 | 20.0 | 26.0 |
| Magnesium stearate B.P. | 1.0 | 2.0 | 2.5 |
| | 200.0 | 350.0 | 500.0 |

*Incorporates 50% overage

Tablets of the above compositions are made by the following process:

1. Screen and mix the drug plus half the lactose and Avicel. Wet granulate with water, dry and dryscreen.
2. Mix the vitamins, tartaric acid and remaining lactose and Avicel plus half the magnesium stearate. Slug on a suitable machine, dry screen.
3. Mix the granules from part 1 and 2, add the Explotab and remaining magnesium stearate and mix. Compress on a compression machine.

EXAMPLES 10 TO 12

| Capsules | Example 10 10 mg base | Example 11 20 mg base | Example 12 50 mg base |
|---|---|---|---|
| 2,3,4,10-tetrahydro-3,3-dimethyl-10-phenyl-pyrimido[1,2-a]indol-10-ol mesylate | 13.29 | 26.58 | 66.45 |
| Nicotinamide B.P. | 30.0 | 30.0 | 30.0 |
| Pyridoxine HCl B.P | 2.0 | 2.0 | 2.0 |
| Riboflavine B.P. | 6.0* | 6.0* | 6.0* |
| Thiamine Hydrochloride B.P | 7.5* | 7.5* | 7.5* |
| Tartaric acid B.P. powder | 1.0 | 2.0 | 2.0 |
| Lactose B.P. | 41.835 | 95.17 | 123.175 |
| Maize starch dried B.P. | 45.0 | 75.0 | 105.0 |
| Aerosil 200 (colloidal silicon dioxide) | 0.375 | 0.75 | 0.875 |
| Magnesium Stearate B.P. | 150.0 | 250.0 | 350.0 |
| Capsule Sizes | No. 4 | No. 2 | No. 0 |

Capsules containing the above compositions are produced by screening and mixing all ingredients and then filling the mixture into hard gelatin capsules.

EXAMPLE 13

(a)

(−)-2,3,4,10-Tetrahydro-3,3-dimethyl-10-phenyl-pyrimido[1,2-a]indol-10-ol 2,3,4,10-Tetrahydro-3,3-dimethyl-10-phenyl-pyrimido[1,2-a]indol-10-ol(8 g) and natural L(±) tartaric acid (4.1 g) were dissolved in ethanol and left to crystallise slowly. The resulting crystals were filtered off, and the mother liquors reduced in volume and a second crop obtained. The combined crops were recrystallised to constant optical rotation affording, after conversion to the free base, (−)-2,3,4,10-tetrahydro-3,3-dimethyl-10-phenylpyrimido [1,2-a]indol-10-ol $[\alpha_D^{25}]$-212° (0.85% in CHCl$_3$). This was converted to the mesylate salt mp 243°–244° $[\alpha]_D^{24}$-36° [0.77% in MeOH]

(b)

(±)-2,3,4,10-Tetrahydro-3,3-dimethyl-10-phenyl-pyrimido [1,2a]indol-10-ol

The mother liquors from the above experiment were concentrated and the (+) enriched base obtained. In a similar way the salt with unnatural D(−) tartaric acid was obtained which after recrystallisation to constant rotations and conversion to the free base gave 1.5 g of the (+) isomer $[\alpha]_D^{25}$+223° (0.88% in CHCl$_3$). This was then converted to the mesylate salt m.p. 241°–242° $[\alpha]_D^{25}$+37° (c 1% in MeOH). The enantiomers were shown to be >98% pure by NMR using Pr(Opt)$_3$ shift reagent.

We claim:

1. A method of treating or preventing obesity in mammals which comprises orally administering to a mammal in need thereof an amount effective to reduce weight gain or cause weight loss, as desired, in said mammal of 2,3,4,10-tetrahydro-3,3-dimethyl-10-phenyl-pyrimido[1,2-a]indole-10-ol or a pharmaceutically acceptable acid addition salt thereof.

2. A method as claimed in claim 1 wherein the anti-obesity agent is (−)-2,3,4,10-tetrahydro-3,3-dimethyl-10-phenylpyrimido[1,2-a]indol-10-ol or a pharmaceutically acceptable acid addition salt thereof.

3. A method as claimed in claim 1 or 2 wherein the anti-obesity agent is administered with a pharmaceutically acceptable carrier in the form of a pharmaceutical composition.

* * * * *